(12) United States Patent
Owen et al.

(10) Patent No.: US 8,449,825 B2
(45) Date of Patent: *May 28, 2013

(54) HIGH THROUGHPUT SCREEN

(75) Inventors: David Geraint Owen, Cambridge (GB); Nicholas Gerard Byrne, Cambridge (GB)

(73) Assignee: Xention Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/940,564

(22) Filed: Nov. 5, 2010

(65) Prior Publication Data

US 2011/0048939 A1    Mar. 3, 2011

Related U.S. Application Data

(63) Continuation of application No. 11/133,808, filed on May 20, 2005, now Pat. No. 7,846,389, which is a continuation of application No. 09/719,236, filed as application No. PCT/GB99/01871 on Jun. 14, 1999, now Pat. No. 6,936,462.

(30) Foreign Application Priority Data

Jun. 12, 1998   (GB) .................................. 9812783.0

(51) Int. Cl.
*G01N 27/00*   (2006.01)
(52) U.S. Cl.
USPC ... 422/82.01; 422/82.02; 435/7.2; 435/283.1; 435/288.4; 435/288.5
(58) Field of Classification Search
USPC ................. 422/82.01, 82.02, 101, 102, 103, 422/104; 435/7.2, 283.1, 288.4, 288.5
See application file for complete search history.

(56) References Cited

U.S. PATENT DOCUMENTS

| 3,799,743 | A | 3/1974 | Alexander et al. |
| 3,856,633 | A | 12/1974 | Fletcher, III |

(Continued)

FOREIGN PATENT DOCUMENTS

| DE | 19605830 | 2/1997 |
| DE | 19628928 | 1/1998 |

(Continued)

OTHER PUBLICATIONS

Pantoja, Rigo, Sigg, Daniel, Blunck, Rikard, Bezanilla, Francisco, and Heath, James R. (2001) "Bilayer Reconstitution of Voltage-Dependent Ion Channels Using a Microfabricated Silicon Chip," Biophysical Journal, vol. 81, Oct. 2001, pp. 2389-2394.

(Continued)

*Primary Examiner* — Melanie Y Brown
(74) *Attorney, Agent, or Firm* — Downs Rachlin Martin PLLC

(57) ABSTRACT

The present invention relates to a structure comprising a biological membrane and a porous or perforated substrate, a biological membrane, a substrate, a high throughput screen, methods for production of the structure membrane and substrate, and a method for screening a large number of test compounds in a short period. More particularly it relates to a structure comprising a biological membrane adhered to a porous or perforated substrate, a biological membrane capable of adhering with high resistance seals to a substrate such as perforated glass and the ability to form sheets having predominantly an ion channel or transporter of interest, a high throughput screen for determining the effect of test compounds on ion channel or transporter activity, methods for manufacture of the structure, membrane and substrate, and a method for monitoring ion channel or transporter activity in a membrane.

21 Claims, 7 Drawing Sheets

U.S. PATENT DOCUMENTS

| | | | |
|---|---|---|---|
| 4,055,799 A | 10/1977 | Coster et al. |
| 4,062,750 A | 12/1977 | Butler |
| 4,071,315 A | 1/1978 | Chateau |
| 4,111,754 A | 9/1978 | Park |
| 4,128,456 A | 12/1978 | Lee et al. |
| 4,225,410 A | 9/1980 | Pace |
| 4,441,507 A | 4/1984 | Steffin |
| 4,456,522 A | 6/1984 | Blackburn |
| 4,490,216 A | 12/1984 | McConnell |
| 4,510,442 A | 4/1985 | Neher |
| 4,661,235 A | 4/1987 | Krull et al. |
| 4,803,154 A | 2/1989 | Uo et al. |
| 4,874,499 A | 10/1989 | Smith et al. |
| 4,894,343 A | 1/1990 | Tanaka et al. |
| 4,897,426 A | 1/1990 | Linas et al. |
| 4,911,806 A | 3/1990 | Hofmann |
| 4,912,060 A | 3/1990 | Fein |
| 4,952,518 A | 8/1990 | Johnson et al. |
| 5,001,048 A | 3/1991 | Taylor et al. |
| 5,009,846 A | 4/1991 | Gavet et al. |
| 5,026,649 A | 6/1991 | Lyman et al. |
| 5,041,266 A | 8/1991 | Fox |
| 5,110,556 A | 5/1992 | Lyman et al. |
| 5,111,221 A | 5/1992 | Fare et al. |
| 5,169,600 A | 12/1992 | Ishizaka et al. |
| 5,187,096 A | 2/1993 | Giaever et al. |
| 5,225,374 A | 7/1993 | Fare et al. |
| 5,229,163 A | 7/1993 | Fox |
| 5,234,566 A | 8/1993 | Osman et al. |
| 5,262,128 A | 11/1993 | Leighton et al. |
| 5,283,194 A * | 2/1994 | Schmukler ............. 435/285.2 |
| 5,290,700 A | 3/1994 | Binot et al. |
| 5,368,712 A | 11/1994 | Tomich et al. |
| 5,378,342 A | 1/1995 | Ikematsu et al. |
| 5,443,955 A | 8/1995 | Cornell et al. |
| 5,460,945 A | 10/1995 | Springer et al. |
| 5,470,743 A | 11/1995 | Mussi et al. |
| 5,506,141 A | 4/1996 | Weinreb et al. |
| 5,508,200 A | 4/1996 | Tiffany et al. |
| 5,510,628 A | 4/1996 | Georger, Jr. et al. |
| 5,521,702 A | 5/1996 | Salamon et al. |
| 5,547,833 A | 8/1996 | Dorval et al. |
| 5,563,067 A | 10/1996 | Sugihara et al. |
| 5,583,037 A | 12/1996 | Mussi et al. |
| 5,605,662 A | 2/1997 | Heller et al. |
| 5,632,957 A | 5/1997 | Heller et al. |
| 5,643,796 A | 7/1997 | Van den Engh et al. |
| 5,741,463 A * | 4/1998 | Sanadi ............. 422/527 |
| 5,750,015 A | 5/1998 | Soane et al. |
| 5,780,752 A | 7/1998 | Okubo et al. |
| 5,810,725 A | 9/1998 | Sugihara et al. |
| 5,889,216 A | 3/1999 | Okubo et al. |
| 5,904,824 A | 5/1999 | Oh |
| 5,911,871 A | 6/1999 | Preiss et al. |
| 5,955,352 A | 9/1999 | Inoue et al. |
| 5,958,345 A | 9/1999 | Turner et al. |
| 5,981,268 A | 11/1999 | Kovacs et al. |
| 6,015,714 A | 1/2000 | Baldarelli et al. |
| 6,032,062 A | 2/2000 | Nisch |
| 6,048,722 A | 4/2000 | Farb et al. |
| 6,056,861 A | 5/2000 | Fuhr et al. |
| 6,063,260 A | 5/2000 | Olesen et al. |
| 6,064,260 A | 5/2000 | Montgomery et al. |
| 6,068,818 A | 5/2000 | Ackley et al. |
| 6,093,296 A | 7/2000 | Soane et al. |
| 6,099,803 A | 8/2000 | Ackley et al. |
| 6,103,479 A | 8/2000 | Taylor |
| 6,113,768 A | 9/2000 | Fuhr et al. |
| 6,117,291 A | 9/2000 | Olesen et al. |
| 6,132,582 A | 10/2000 | King et al. |
| 6,143,496 A | 11/2000 | Brown et al. |
| 6,151,519 A | 11/2000 | Sugihara et al. |
| 6,156,181 A | 12/2000 | Parce et al. |
| 6,163,719 A | 12/2000 | Sherman |
| 6,207,031 B1 | 3/2001 | Adourian et al. |
| 6,225,059 B1 | 5/2001 | Ackley et al. |
| 6,228,326 B1 | 5/2001 | Boxer et al. |
| 6,235,520 B1 | 5/2001 | Malin et al. |
| 6,267,872 B1 | 7/2001 | Akeson et al. |
| 6,277,629 B1 | 8/2001 | Wolf et al. |
| 6,284,113 B1 | 9/2001 | Bjornson et al. |
| 6,287,517 B1 | 9/2001 | Ackley et al. |
| 6,315,940 B1 | 11/2001 | Nisch et al. |
| 6,329,209 B1 | 12/2001 | Wagner et al. |
| 6,355,491 B1 | 3/2002 | Zhou et al. |
| 6,368,851 B1 | 4/2002 | Baumann et al. |
| 6,377,057 B1 | 4/2002 | Borkholder |
| 6,379,916 B1 | 4/2002 | Meyer |
| 6,403,367 B1 | 6/2002 | Cheng et al. |
| 6,455,007 B1 | 9/2002 | Mansky et al. |
| 6,470,226 B1 | 10/2002 | Olesen et al. |
| 6,472,144 B2 | 10/2002 | Malin et al. |
| 6,475,760 B1 | 11/2002 | Baumann et al. |
| 6,475,808 B1 | 11/2002 | Wagner et al. |
| 6,488,829 B1 | 12/2002 | Schroeder et al. |
| 6,638,743 B2 | 10/2003 | Baumann et al. |
| 6,682,649 B1 | 1/2004 | Petersen et al. |
| 6,686,193 B2 | 2/2004 | Maher et al. |
| 6,699,665 B1 | 3/2004 | Kim et al. |
| 6,758,961 B1 | 7/2004 | Vogel et al. |
| 6,878,344 B2 | 4/2005 | Mansky et al. |
| 2001/0005489 A1 | 6/2001 | Roach et al. |
| 2001/0005774 A1 | 6/2001 | Kato et al. |
| 2001/0045359 A1 | 11/2001 | Cheng et al. |
| 2002/0006357 A1 | 1/2002 | McGeoch et al. |
| 2002/0025575 A1 | 2/2002 | Malin et al. |
| 2002/0074227 A1 | 6/2002 | Nisch et al. |
| 2002/0115196 A1 | 8/2002 | Boven et al. |
| 2002/0119579 A1 | 8/2002 | Wagner |
| 2002/0137121 A1 | 9/2002 | Rubinsky et al. |
| 2002/0155586 A1 | 10/2002 | Cheng et al. |
| 2003/0026738 A1 | 2/2003 | Everett |
| 2003/0059936 A1 | 3/2003 | Baumann et al. |
| 2003/0124029 A1 | 7/2003 | Webb et al. |
| 2005/0148064 A1 | 7/2005 | Yamakawa et al. |
| 2005/0226784 A1 | 10/2005 | Kobayashi |

FOREIGN PATENT DOCUMENTS

| | | |
|---|---|---|
| DE | 19646505 | 5/1998 |
| DE | 19712309 | 5/1998 |
| DE | 19744649 | 4/1999 |
| DE | 19841337 | 9/1999 |
| EP | 0094193 | 8/1987 |
| EP | 0299778 | 1/1989 |
| EP | 0299779 | 1/1989 |
| EP | 01620907 | 1/1992 |
| EP | 0639768 | 2/1995 |
| EP | 0441120 | 4/2002 |
| FR | 2659347 | 9/1991 |
| JP | 4-338240 | 11/1992 |
| JP | 05038281 | 2/1993 |
| JP | 09211010 | 8/1997 |
| WO | 85/02201 | 5/1985 |
| WO | 89/01159 | 2/1989 |
| WO | 9002327 | 3/1990 |
| WO | 91/13977 | 9/1991 |
| WO | 94/25862 | 11/1994 |
| WO | 96/10454 | 4/1996 |
| WO | 96/12957 | 5/1996 |
| WO | 96/13721 | 5/1996 |
| WO | 96/36436 | 11/1996 |
| WO | 97/17426 | 5/1997 |
| WO | 97/20203 | 6/1997 |
| WO | 97/25616 | 7/1997 |
| WO | 97/49987 | 12/1997 |
| WO | 9745730 | 12/1997 |
| WO | 98/22819 | 5/1998 |
| WO | 98/23948 | 6/1998 |
| WO | 98/47003 | 10/1998 |
| WO | 98/50791 | 11/1998 |
| WO | 98/55870 | 12/1998 |
| WO | 98/58248 | 12/1998 |
| WO | 99/19729 | 4/1999 |
| WO | 99/28037 | 6/1999 |
| WO | 99/66329 | 12/1999 |

| | | |
|---|---|---|
| WO | 00/34776 | 6/2000 |
| WO | 01/71349 | 9/2001 |
| WO | 01/94939 | 12/2001 |

OTHER PUBLICATIONS

Suzuki, Hiroaki, and Takeuchi, Shoji. (2008) "Microtechnologies for Membrane Protein Studies." Anal Bioanal Chem, 391:2695-2702, 2698.

Denyer, Jane, Worley, Jennings, Cox, Brian, Allenby, Gary, and Banks, Martyn. (1998) "HTS Approaches to Voltage-Gated Ion Channel Drug Discovery." Drug Disc. T., vol. 3, No. 7, Jul. 1998, pp. 323-332.

Xu, Jia, Wang, Xiaobo, Ensign, Brooks, Li, Min, Wu, Lei, Guia, Antonio, and Xu, Junquan. (2001) "Ion-Channel Assay Technologies: Quo Vadis?" Drug Disc. T., vol. 6, No. 24, Dec. 2001, pp. 1278-1287.

Thurow, Kerstin, and Weimann, Hilmar, Ph.D. (2007) "Automation Highlights From the Literature." J. Assoc. Laboratory Automation, Drug Disc. T., vol. 12, No. 5, Oct. 2007, pp. 255-259.

Chen, Peihua, Zhang, Wei, Zhou, Jun, Wang, Ping, Xiao, Lidan, and Yang, Mo. (2008) "Development of Planar Patch Clamp Technology and Its Application in the Analysis of Cellular Electrophysiology." Prog Nat Sci, doi: 10.1016/j.pnsc.2008.06.012, vol. 19, pp. 153-160, published online on Dec. 5, 2008.

Kryshtal, O.A., and Pidoplichko, V.I. (1975) "Intracellular Perfusion of Helix Giant Neurons." A.A. Bogomolets Institute of Physiology, Academy of Sciences of the Ukrainian SSR., Kiev. Translated from Neirofiziologiya, vol. 7, No. 3, pp. 327-329, May-Jun. 1975.

The Axon Guide for Electrophysiology and Biophysics Laboratory Techniques, Axon Instruments, Inc. Jun. 1993, http://www.moleculardevices.com/pp./instruments/axon_guide.html. (Jun. 1993).

Williams, A.J. (1994). An Introduction to the Methods Available for Ion Channel Reconstitution, the Plymouth Workshop Handbook, Second Ed. Editor Ogden, D. Cambridge, UK.

Favre, I., Sun, Ye-Ming, Moczydlowski, E., (1999), Reconstitution of Native and Cloned Channels into Planar By-Layers, Methods, Enzymol, 294, 287-304.

Aidley et al. (1996) "Investigating Channel Activity" in Ion Channels: Molecules in Action, pp. 33-57, Cambridge University Press, Cambridge, Great Britain.

Akashi et al. (1996) "Preparation of Giant Liposomes in Physiological Conditions and Their Characterization Under an Optical Microscope," Biophysical Journal vol. 71(6), pp. 3242-3250.

Alberts et al. (1994) Molecular Biology of the Cell, Third Edition, Garland Publishing, New York, pp. 178-191.

Bertl (1989) Current-Voltage Relationships of a Sodium-Sensitive Potassium Channel in the Tonoplast of Chara Corallina, Journal of Membrane Biology, vol. 109, pp. 9-19.

Bridges et al. (1990) "Reconstitution of Epithelial Ion Channels." Current Topics in Membranes and Transport, vol. 37, pp. 283-312.

Cahalan et al. (1992) "Patch Clamp Techniques: An Overview," Methods in Enzymology, vol. 207, pp. 3-14.

Carter (1967) "Haptotaxis and the Mechanism of Cell Motility," Nature 213(73), pp. 256-260.

Cohen, F., Zimmerberg, J., Finkelstein, A. (1980) "Fusion of Phospholipid Vesicles with Planar Phospholipid Bilayer Membranes," J. Gen. Physiol. vol. 75(3), pp. 241-250.

Criado et al. (1987) "A Membrane Fusion Strategy for Single-Channel Recordings of Membranes Usually Non-Accessible to Patch-Clamp Pipette Electrodes," FEBS Letters vol. 224(1), pp. 172-176.

Edelstein et al. (1997) "Single Binding Versus Single Channel Recordings: A New Approach to Study Ionotropic Receptors," Biochemistry vol. 36(45), pp. 13755-13760.

Edwards (Feb. 25, 2000; 2:09 pm EST) Cal. Researchers Make 'Bionic Chip' Associated Press.

Ehrlich (1992) "Planar Lipid Bilayers on Patch Pipettes: Bilayer Formation and Ion Channels Incorporation," Methods in Enzymology vol. 207, pp. 463-470.

Eray et al. (1995) "A Highly Stable and Selective Biosensor Using Modified Nicotinic Acetylcholine Receptor (nAChR)." BioSystems vol. 35(2-3), pp. 183-188.

Hodgson (1992) "Receptor Screening and the Search for New Pharmaceuticals." Bio/Technology vol. 10(9), pp. 973-980.

Horn et al. (1988) "Muscarinic Activation of Ionic Currents Measured by a New Whole-Cell Recording Method." Journal of General Physiology vol. 92(2), pp. 145-159.

Huang et al. (Feb. 1999) "A Microfabricated Chip for the Study of Cell Electroporation." Biomedical Engineering Laboratory, Department of Mechanical Engineering, University of California, Berkeley, CA 94720.

Hub et al. (1982) "Preparation of Large Unilamellar Vesicles," FEBS Letters, vol. 140(2), pp. 254-256.

Keller et al. (1988) "Single Channel Recordings of Reconstituted Ion Channel Proteins: An Improved Technique." Pflugers Arch. vol. 411(1), pp. 94-100.

Kelly et al. (1996) "Ion Channels from Synaptic Vesicle Membrane Fragments Reconstituted into Lipid Bilayers." Biophysical Journal vol. 70(6): 2593-9.

Kostyuk et al. (1975) "Effect of Internal Fluoride and Phosphate on Membrane Currents During Intracellular Dialysis of Nerve Cells." Nature 257 (5528): 691-693.

Kostyuk et al. (1984) Intracellular Perfusion of Excitable Cells, pp. 35-51, John Wiley & Sons, Inc. NY.

Labarca et al. (1992) "Insertion of Ion Channels into Planar Lipid Bilayers by Vesicle Fusion." Methods in Enzymology vol. 207, pp. 447-463.

Lewis et al. (1990) "Patch Clamp of Cation Channels," Current Topics in Membranes and Transport vol. 37, pp. 215-246.

Masuda et al. (1989) "Novel Method of Cell Fusion in Field Constriction Area in Fluid Integrated Circuit." IEEE Trans. IAS vol. 25, pp. 732-737.

Mazia et al. (1975) "Adhesion of Cells to Surfaces Coated with Polylysine," Journal of Cell Biology vol. 66, pp. 198-200.

Mrksich et al. (Oct. 1996) "Controlling Cell Attachment on Contoured Surfaces with Self-Assembled Monolayers of Alkanethiolates on Gold." Proc. Natl. Acad. Sci. USA, vol. 93, pp. 10775-10778.

Mrksich et al. (Jun. 1995) "Patterning Self-Assembled Monolayers Using Microcontact Printing: A New Technology for Biosensors?" TBTech vol. 13, pp. 228-235.

Mueller et al. (1983) "Formation and Properties of Cell-Size Lipid Bilayer Vesicles." Biophysical Journal vol. 44, pp. 375-381.

Nollert et al. (1995) "Lipid Vesicle Adsorption Versus Formation of Planar Bilayers on Solid Surfaces." Biophysical Journal vol. 69(4), pp. 1447-1455.

Rae et al. (1991) "Low Access Resistance Perforated Patch Recordings Using Amphotericin B." Journal of Neuroscience Methods vol. 37(1), pp. 15-26.

Roberts et al. (1992) "Patch Voltage Clamping with Low-Resistance Seals: Loose Patch Clamp." Methods in Enzymology vol. 27, pp. 155-176.

Schurholz (1996) "Critical Dependence of the Solubilization of Lipid Vesicles by the Detergent CHAPS on the Lipid Composition. Functional Reconstitution of the Nicotinic Acetylcholine Receptor Into Performed Vesicles Above the Critical Micellization Concentration." Biophysical Chemistry, vol. 58, pp. 87-96.

Schurholz et al. (1992) "Functional Reconstitution of the Nicotinic Acetylcholine Receptor by CHAPS Dialysis Depends on the Concentrations of Salt, Lipid, and Protein." Biochemistry vol. 31(21), pp. 5067-5077.

Wonderlin et al. (1990) "Optimizing Planar Lipid Bilayer Single-Channel Recordings for High Resolution with Rapid Voltage Steps." Biophysics Journal vol. 58, pp. 289-297.

Woodbury (1999) "Nystatin/Ergosterol Method for Reconstituting Ion Channels into Planar Lipid Bilayers." Methods in Enzymology vol. 294, pp. 319-339.

Yoshii et al. (1984) "Perfusion of Oocytes" in Intracellular Perfusion of Excitable Cells, pp. 77-89.

Edry-Schiller et al. (1991) "A Bursting Potassium Channel in Isolated Cholinergic Synaptosomes of Torpedo Electric Organ." Journal of Physiology vol. 439, pp. 627-647.

Kyrozis et al. (1995) "Perforated-patch recording with gramicidin avoids artifactual changes in intracellular chloride concentration." Journal of Neuroscience Methods vol. 57, pp. 27-35.

Nichols et al. (1990) "The Regulation of ATP-Sensitive K+ Channel Activity in Intact and Permeabilized rat Ventricular Myocytes." Journal of Physiology vol. 423, pp. 91-110.

Yelin et al. (1995) "The Pharmacological Profile of the Vesicular Monoamine Transporter Resembles that of Multidrug Transporters." FEBS Letters 377, pp. 201-207.

EPO Communication and Search Report dated Dec. 5, 2005 for related application No. 05076930.6.

Ma et al., "Effects of ADP, DTT, and Mg2+ on the ion-conductive property of chloroplast H+-ATPase (CF0-CF1) reconsitituted into bilayer membrane", Mar. 17, 1997, Biochem. And Biophus. Res. Comm., 232(2): pp. 461-163.

Chan et al., "Cation and anion channels in rat and human spermatozoa", 1997, Biochim. et Bioph. Acta, 1323(1): pp. 117-129.

Anderson, M.T., et al., "Simultaneous fluorescence-activated cell sorter analysis of two distinct transcriptional elements within a single cell using engineered green fluorescent proteins," Proc. Nat'l. Acad. Sci. USA, vol. 93, pp. 8508-8511 (1996).

Brew, H. and Attwell, D., "Electrogenic glutamate uptake is a major current carrier in the membrane of axolotl retinal glial cells" Nature, 327, pp. 707-709 (1987).

Fu, Anne Y. et al., "A microfabricated fluorescence-activated cell sorter," Nature Biotechnology, vol. 17, pp. 1109-1111 (1999).

Hamill, O.P., Marty a., Neher, E., Sakmann, B. & Sigworth, F.J. "Improved patch-clamp techniques for high-resolution recording from cells and cell-free membrane patched", Pfluger's Archives, 391, pp. 85-100 (1981).

"Lecture 5: Electrophysiological Techniques", BIOL 445—1997 Notes on the WWW http://biology.queensu.ca/courses/bio445/lect5.html.

Margolsee, R.F., McHendry-Rinde, B., and Horn, R., "Panning transfected cells for electrophysiological studies", Biotechniques, 15, pp. 906-911 (1993).

Sheng, M., "PDZs and receptor/channel clustering: rounding up the latest suspects." Neuron, vol. 17, pp. 575-578, Oct. 1996.

Winegar, Bruce, "Obtaining Gigaohm Seals" Eleusis Patch Clamp Resources (1999).

Hille, B. (ed.) "Ionic Channels of Excitable Membranes." pp. 1-20; 140-169; 202-235 (1992), 2nd Edition, Sinauer Associates, Inc., Sunderland, MA.

Sinauer Associates, Sunderland. Sakmann, B. & Neher, E. (eds). "Single Channel Recording," Plenum Press, New York and London, pp. 3-30; 307-327 (1995).

Stephens et al. On the Mechanism of 4-Aminopyridine Action on the Cloned Mouse Brain Potassium Channel mkv1.1, Journal of Physiology, 1994, 477(2): pp. 187-196.

M. Goulian et al., "Gramicidin Channel Kinetics Under Tension," Biophysical Journal, vol. 74, pp. 328-337, (Jan. 1998).

Kyle et al. "Characterization of three-dimensional tissue cultures using electrical impedance spectroscopy," Biophysical Journal, vol. 76, May 1999, pp. 2640-2648.

* cited by examiner

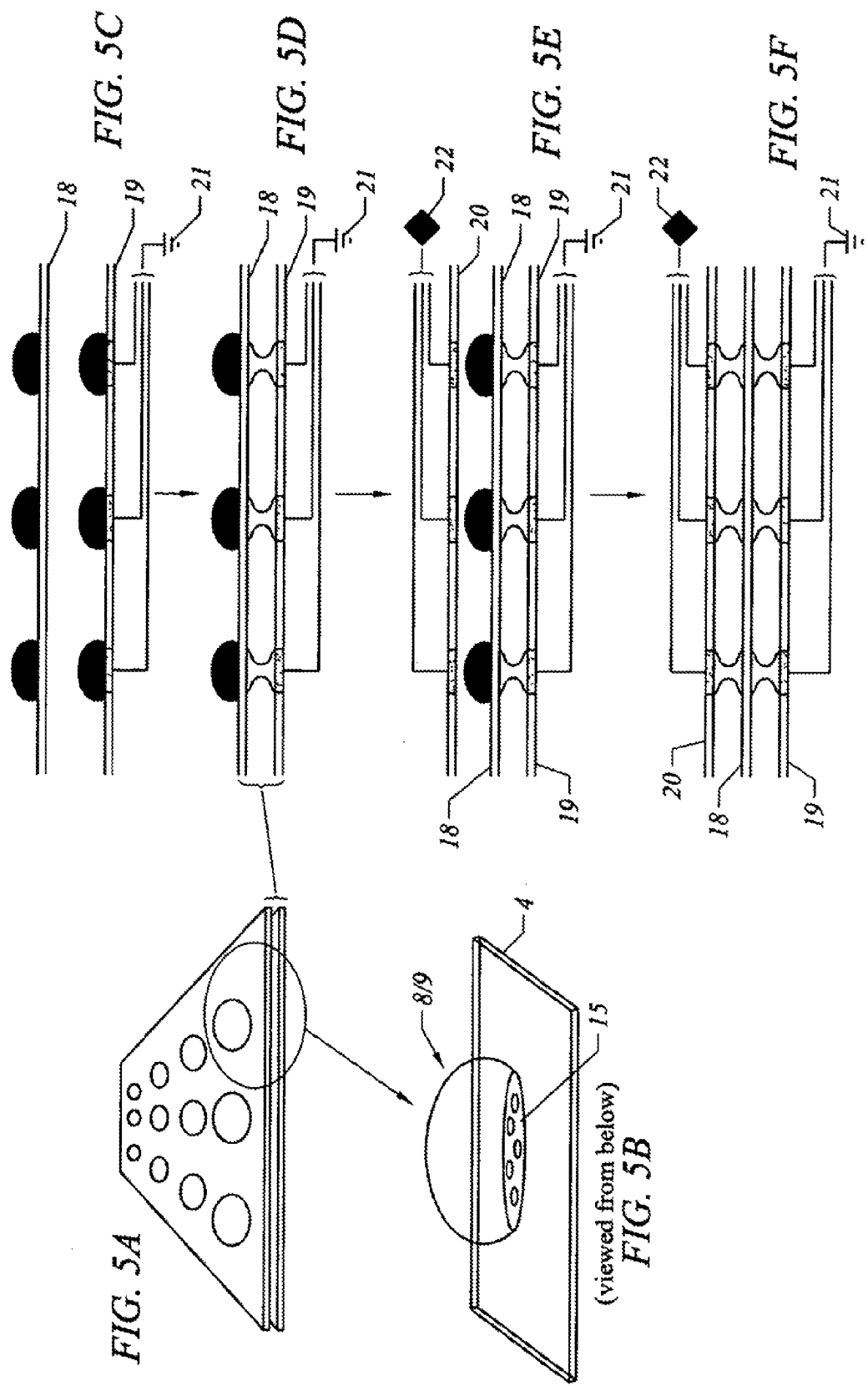

HIGH THROUGHPUT SCREEN

CROSS REFERENCE TO RELATED APPLICATIONS

This application is a continuation of U.S. application Ser. No. 11/133,808, filed May 20, 2005, now U.S. Pat. No. 7,846,389 which is a continuation of U.S. application Ser. No. 09/719,236, filed Apr. 19, 2001, now U.S. Pat. No. 6,936,462, and claims priority of UK Application No. 9812783.0, filed on Jun. 12, 1998, and International Application No. PCT/GB99/01871, filed Jun. 14, 1999, the disclosures of which are incorporated fully herein by reference.

FIELD OF THE INVENTION

The present invention relates to a structure comprising a biological membrane and a porous or perforated substrate, a biological membrane, a substrate, a high throughput screen, methods for production of the structure membrane and substrate, and a method for screening a large number of test compounds in a short period. More particularly it relates to a structure comprising a biological membrane adhered to a porous or perforated substrate, a biological membrane capable of adhering with high resistance seals to a substrate such as perforated glass and the ability to form sheets having predominantly an ion channel or transporter of interest, a high throughput screen for determining the effect of test compounds on ion channel or transporter activity, methods for manufacture of the structure, membrane and substrate, and a method for monitoring ion channel or transporter activity in a membrane.

BACKGROUND OF THE INVENTION

Ion channels are transmembrane proteins which form pores in the membrane which allow ions to pass from one side to the other. Hille, B (ed). *Ionic channels of excitable membranes.* 1992. They may show ion specificity, allowing specific ions to passively diffuse across a membrane down their electrochemical gradients. Although certain types of channels are on the average open all the time and at all physiological membrane potentials (so-called leak channels), many channels have 'gates' which open in response to a specific perturbation of the membrane. Perturbations known to cause opening of ion channels include a change in the electric potential across the membrane (voltage-gated channels), mechanical stimulation (mechanically-gated channels) or the binding of a signalling molecule (ligand-gated channels).

Transporters are proteins in the cell membrane which catalyse the movement of inorganic ions such as $Na^+$ and $K^+$ as well as organic molecules such as neurotransmitters as in the case of so-called re-uptake pumps, e.g. GABA, dopamine and glycine. Two distinguishing features of carriers versus pores are i) their kinetics-movement of ions via transporters is very much slower than the $>10^6$ ions per second that is encountered with ion channels and ii) ion channels conduct down electrochemical gradients whereas transporters can 'pump' uphill i.e. against concentration gradients (Hille, 1992). The latter process is normally directly dependent upon energy being provided in a stoichiometric fashion.

Ion channel activity has been studied using a technique referred to as "patch clamping." Hamill, O. P., Marty A., Neher, E., Sakmann, B. & Sigworth, F. J. (1981). Improved patch-clamp techniques for high-resolution current recording from cells and cell-free membrane patches. *Pfluger's Archives,* 391, 85-100. According to this technique a small patch of cell membrane is generally isolated on the tip of a micropipette by pressing the tip against the membrane. It has been suggested that if a tight seal between the micropipette and the patch of membrane is established electric current may pass through the micropipette only via ion channels in the patch of membrane. If this is achieved the activity of the ion channels and their effect on membrane potential, resistance and current may be monitored. If the electric potential across the membrane remains constant the current supplied to it is equal to the current flowing through ion channels in the membrane. If ion channels in the membrane close, resistance of the membrane increases. If the current applied remains constant the increase of resistance is in direct proportion to an increase of electric potential across the membrane.

Many drugs are known to exert their effect by modulation of ion channels, but the development of novel compounds acting on them is hampered considerably by the difficulty of screening at high-throughput rates for activity. Conventional electrophysio-logical methods such as patch or voltage clamp techniques provide definitive mechanistic information but suffer from the problem that they are unsuited to the rapid screening of test compounds.

WO96/13721 describes apparatus for carrying out a patch clamp technique utilized in studying the effect of certain materials on ion transfer channels in biological tissue. It discloses patch clamp apparatus utilizing an autosampler, such as those utilized with HPLC apparatus, to provide a higher throughput than may be achieved by the conventional patch clamp technique. This apparatus suffers from the problems that it merely semi-automates the drug delivery system, not the patch clamp recording. It therefore suffers from the same limitations as traditional patch-clamping with respect to speed of processing compounds and can in no way be considered a high-throughput system. The system still requires linear processing (i.e. processing of data obtained for one cell after another). In direct contrast the invention described herein provides parallel processing and thus genuine high-throughput of compounds.

The term "biological membrane" used herein is taken to include artificial membranes such as lipid bilayers and other membranes known to a person skilled in the art. Within the context of this specification the word "comprises" is taken to mean "includes" and is not intended to mean "is limited to only".

SUMMARY OF THE INVENTION

The present invention relates to a structure comprising a biological membrane and a porous or perforated substrate, a biological membrane, a substrate, a high throughput screen, methods for production of the structure membrane and substrate, and a method for screening a large number of test compounds in a short period. More particularly it relates to a structure comprising a biological membrane adhered to a porous or perforated substrate, a biological membrane capable of adhering with high resistance seals to a substrate such as perforated glass and the ability to form sheets having predominantly an ion channel or transporter of interest, a high throughput screen for determining the effect of test compounds on ion channel or transporter activity, methods for manufacture of the structure, membrane and substrate, and a method for monitoring ion channel or transporter activity in a membrane.

BRIEF DESCRIPTION OF THE DRAWINGS

The invention will now be described by reference to the following examples of preferred embodiments and accompanying drawings in which:

FIG. 5 shows an embodiment of a fluid matrix system wherein an array of miniature recording chambers are created by dispensing droplets on to the recording substrate in a pre-determined pattern and density. FIG. 5(f) shows the full sandwich (recording configuration) of the system.

DETAILED DESCRIPTION OF THE PREFERRED EMBODIMENTS

Figure 1A:
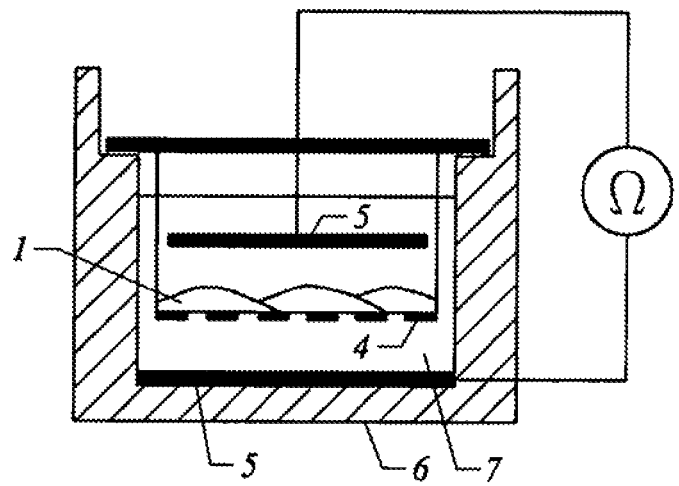
FIG. 1 shows an epithelial cell version of a screen according to an embodiment of the invention.

The present invention addresses the problems associated with the known screens and screening methods. The invention has application principally in the measurement of ion channel activity but also of transporters where these are electrogenic e.g. $Na^+/K^+$; $Na^+/Ca2^+$; glutamate re-uptake transporter. Brew, H. & Attwell, D. (1987). Electrogenic glutamate uptake is a major current carrier in the membrane of axilotl retinal glial cells. *Nature*, 327, 707-9.

In the various embodiments shown in the figures, the following components are identified by the following reference numerals:

| | |
|---|---|
| 1 | cells |
| 2 | permeabilized cell surface |
| 3 | voltage clamp |
| 4 | porous substrate |
| 5 | electrode |
| 6 | well wall |
| 7 | solution perfusion channel |
| 8 | cell line or primary cell |
| 9 | permeabilized cell |
| 10 | multiwell plate (e.g. 96 wells) |
| 11 | integral recording head cluster |
| 12 | multiplexer |
| 13 | ADC/computer |
| 14 | fluid level |
| 15 | pore |
| 16 | O-ring |
| 17 | recording assembly |
| 18 | cell plate |
| 19 | reference plate |
| 20 | recording plate |
| 21 | reference electrode |
| 22 | recording electrode |
| 23 | "demi-sandwich" |
| 24 | full sandwich (recording configuration) |

In a first aspect the present invention provides a structure which comprises a biological membrane adhered with a high resistance seal to a porous or perforated substrate for use in a high through put screen wherein the biological membrane comprises an ion channel or transporter.

In a second aspect the invention provides a biological membrane for use in the structure which is capable of adhering to a substrate with a high resistance seal wherein each cell forms a tight junction with adjacent cells and expresses an ion channel which is localised in the cell membrane.

In a third aspect the invention provides a substrate for use in a high throughput screen which is perforated.

In a fourth aspect the invention provides a high throughput (HiT) screen for the detection and assay of test compounds with activity on voltage gated ion channels which comprises the biological membrane.

In a fifth aspect the invention provides a method of manufacturing a structure comprising a biological membrane adhered with a high resistance seal to a perforated substrate which comprises the steps of selecting a substrate, perforating it, introducing a biological membrane to the substrate and sealing each pore with biological membrane.

In a sixth aspect the invention provides a method of manufacturing the biological membrane which comprises the steps of selecting a cell type, evaluating it for ability to form contiguous layers of cells with tight junctions and for low to negligible numbers of voltage gated ion channels, culturing the cells on a substrate and ensuring that a contiguous layer of cells is grown.

In a seventh aspect the invention provides a method of manufacturing a perforated substrate which comprises the steps of shining a laser of preselected focal area, power or time of exposure at a coverslip to perforate it. This method also may include the additional step of modification of the perforated area by exposure to plasma and/or localised heating in order to attain the appropriate level of smoothness of the perforation(s).

In an eighth aspect the invention provides a method of screening for the detection or assay of compounds with activity on ion channels which comprises the steps of placing a biological membrane which expresses ion channels of interest in contact with test compound in physiological solution or non-physiological solution comprising a solvent such as dimethyl sulphoxide and measuring the resistance or impedance of the biological membrane under the influence of test compound.

Preferably an embodiment of the biological membrane comprises cells having an ion channel or transporter which naturally resides in the cell membrane thereof, or it can be inserted by transfection with cDNA and/or cRNA encoding the ion channel or transporter. The invention thus has the advantage that is permits studies of native channels or transporters where the precise subunit composition is unknown or indeed where the molecular identity is completely unknown (i.e. not yet cloned) but also heterologously-expressed cloned channels or transporters where the identity of the native channel or transporter is known or where precise knowledge is required of the interaction of compound structures and chemical moieties of the ion channel or transporter. Therefore the system is substantially more versatile then existing approaches which are insensitive and rely on getting high concentrations of cells (not always possible with neurones) and high signal to noise ratios which limits their use to only certain types of cells and ion channels.

Preferably an embodiment of the biological membrane comprises a plurality of ion channels or transporters which are predominantly preselected ion channels or transporters of interest. This provides the invention with the advantage of permitting parallel screening of different channels potentially providing an even higher throughput of compounds.

More preferably an embodiment of the biological membrane comprises genetically engineered cells which have been engineered to predominantly express an ion channel or transporter.

Preferably the ion channels are voltage gated ion channels.

Preferably an embodiment of the biological membrane comprises cells selected from the group which comprises HEK-293 cells, genetically modified Chinese hamster ovary (CHO) cells, primary neuronal tissue such as hippocampus, dorsal root ganglia, superior cervical ganglia etc.; skeletal muscle; smooth muscle; cardiac muscle; immune cells; epithelia; endothelia etc.

CHO cells and CHO sub-clones such as CHO-KI and CHO-dhfr (also known as Dukx) have exceptionally low levels of endogenous ion channel expression thus providing the advantage of having excellent signal to noise characteristics within a mammalian cell environment. Similarly, HEK-293 (human embryonic kidney) cells express low levels of native channels and provide a human expression 'background'. Both these expression systems are infinitely preferable to the well-used Xenopus oocyte technique where not only are native channels and subunits abundant, but the amphibian cell environment differs in important ways from mammalian cells.

Preferably an embodiment of the biological membrane comprises ion channels having rapid activation and inactivation kinetics which existing methods of high-throughput screening cannot resolve. Existing systems, therefore, average transient ion channel signals frequently over periods of many seconds. Channels inactivating with time-constants of the order of milliseconds and without a steady-state presence are effectively undetectable in such systems. The invention presented here however, has the advantage that it can easily resolve such kinetics just as traditional patch clamping does, but at high-throughput rates.

Preferably an embodiment of the biological membrane comprises ion channels which show specificity for ions selected from the group which comprises sodium, potassium, calcium, chloride.

Preferably an embodiment of the biological membrane comprises a contiguous layer of cells capable of adhering with a high resistance seal to substrates selected from the group which comprises perforated glass, plastics, rubber, polytetraflurotethylene (PTFE), PTFE/glass fabric and polyethylene terephthalate (PETP).

Preferably an embodiment of the biological membrane comprises a pseudo-epithelium wherein one face of a contiguous layer of cells is permeabilized thereby providing access to the interior of the cells. This has the great advantage of providing the means for current and voltage-clamping which is not possible with any existing high-throughput screening system. Not only does this permit high time-resolution recording but it also provides the means to stimulate or activate voltage-gated ion channels in a precise and controlled manner. For example, it is not necessary to alter the ionic composition e.g. by elevating $K^+$ to depolarize cells, which in itself can modulate the kinetics of ion channels (e.g. $K^+$ channels) and also obscure the activity of novel ligands by competition at ion channel binding sites. This is a very great advantage over all existing systems. Permeabilization also allows the introduction to the cytosol of compounds that otherwise could not do so either by virtue of molecular weight or physicochemical characteristics.

Preferably an embodiment of the biological membrane comprises a contiguous layer of cells which is permeabilized by an antibiotic selected from the group which comprises amphotericin and nystatin; or detergent selected from the group which comprises digitonin and saponin; or physical disruption using a high voltage field; or by enzymatic digestion of a part of the membrane using an appropriate enzyme.

An advantage of using high voltage fields to permeabilize the membrane (electropermeabilisation) is that such a technique can permeabilize the plasmamembrane while sparing smaller intracellular structures such as mitochondria and endoplasmic reticulum. The technique can also be controlled very precisely and would not necessitate a facility to exchange solutions in a lower chamber of the recording apparatus.

Preferably an embodiment of the substrate comprises a perforated coverslip.

Preferably an embodiment of the substrate has pores of diameters between 0.5 Φm and 10 Φm. More preferably the pores are of diameters between 1 Φm and 7 Φm. More preferably the diameter is 1-2 Φm.

Preferably an embodiment of the substrate comprises a grid of pores of greater number than 4 but less than 10. This provides the advantage of a statistically acceptable number of parallel recordings (i.e. >4) in each treatment but small enough that the ratio of pores to cells can be made vanishingly small and thus the probability that a pore is sealed with and therefore occluded by a cell extremely high.

Preferably an embodiment of the substrate according to the invention is manufactured of a material selected from the group which comprises glass, plastics, rubber, polytetraflurotethylene (PTFE), PTFE/glass fabric and polyethylene terephthalate (PETP).

Preferably an embodiment of the screen comprises:
- a plurality of chambers, each having a permeable peripheral surface providing a substrate for the biological membrane;
- a plurality of wells each capable of receiving a chamber and a test compound in a physiological solution or non-physiological solution comprising dimethyl sulfoxide (DMSO) or other solvent;
- a plurality of reference electrodes, at least one having electrical contact with each well;
- a movable recording head carrying at least one recording electrode thus providing the basic requirement for automated recording of ion channel activity in a multiwell plate format;
- means for measuring electrical resistance or impedance between the recording and reference electrodes; wherein electrical current may pass between the recording and reference electrodes through the permeable peripheral surface of each chamber only via ion channels or transporters in the biological membrane.

Preferably an embodiment of the screen comprises wells which are provided by a multiwell plate. The advantage of this being that high throughput can be achieved using industry-standard components which can be processed using commercially available automated equipment and robotics. Users will have the possibility of using their existing plate processing equipment thus containing costs in establishing a state-of-the-art high-throughput electrophysiology screen.

Preferably an embodiment of the screen comprises a perforated substrate for the biological membrane.

Preferably a further embodiment of the screen comprises a structure or biological membrane described above having ion channels of interest in an array of droplets on a porous substrate. Preferably an array of miniature recording chambers is created by placing a 'lid' incorporating recording electrodes over the matrix of droplets such that a meniscus of the droplet solution is established. Preferably a test compound in electrically conducting solution is placed in at least one of the droplets or applied via access ports in the 'lid' and the resistance/impedance (in current-clamp configuration) of the biological membrane or conductance (in voltage-clamp configuration) is measured under the influence of the test compound. An advantage of this approach is that sheets of substrate can be designed without the need to transfer pieces of substrate (e.g. discs) to multiwell plates and also obviates complex chamber design with seals, 'O'-rings and the like. The invention can still accommodate addition of solutions and has an additional advantage of using very small volumes and thus small quantities of reagents and cells. Excellent insulation is afforded by the air gaps between adjacent droplets.

Preferably an embodiment of the recording head comprises a single recording electrode capable of being moved to visit each chamber sequentially. More preferably an embodiment of the recording head comprises a plurality of recording electrodes arranged in a line. Even more preferably the recording head comprises a plurality of recording electrodes arranged in a matrix. The advantage of this configuration is that simultaneous recording from all wells is possible via a data-acquisition multiplexing system.

Preferably an embodiment of the screen is capable of multiplexing up to 384 recording elements to a data acquisition system utilizing multiple voltage-clamp amplifiers. This has the advantage of providing extremely high time resolution and effectively simultaneous measurement from all wells. This has the advantage of providing the TERM system with the potential to achieve throughput rates similar to the best possible for conventional fluorescence-based ligand-receptor binding assays ($\geq$150,000 compounds per week).

Preferably an embodiment of the method of manufacturing the structure comprises the steps of simultaneously perforating a coverslip and sealing the pores with biological membrane. This embodiment provides the advantage of eliminating steps in the establishment of the final configuration, namely procedures required to optimise the probability of a cell sealing with pores in the perforated substrate. This has the advantage of simplifying the final product.

Preferably an embodiment of the method of manufacturing the biological membrane includes the step of permeabilizing one surface of the contiguous layer of cells thereby providing access to the interior of the cells. This has the great advantage of providing the means for current and voltage-clamping which is not possible with any existing high-throughput screening system. Not only does this permit high time-resolution recording but is also provides the means to stimulate or activate voltage-gated ion channels in a precise and controlled manner. For example, it is not necessary to alter the ionic composition e.g. by elevating $K^+$ to depolarize cells, which in itself can modulate the kinetics of ion channels (e.g. $K^+$ channels) and also obscure the activity of novel ligands by competition at ion channel binding sites. This is a very great advantage over all existing systems. Permeabilization also allows the introduction to the cytosol of compounds that otherwise could not do so either by virtue of molecular weight or physicochemical characteristics.

Preferably the permeabilization is carried out by the step of contacting the surface with an antibiotic selected from the group which comprises amphotericin and nystatin; or detergent selected from the group which comprises digitonin and saponin; or physical disruption using a high voltage field; or by enzymatic digestion of a part of the cell membrane using an appropriate enzyme.

An advantage of using high voltage fields to permeabilize the membrane (electropermeabilisation) is that such a technique can permeabilize the plasmamembrane while sparing smaller intracellular structures such as mitochondria and endoplamic reticulum. The technique can also be controlled very precisely and would not necessitate a facility to exchange solutions in a lower chamber of the recording apparatus.

Preferably an embodiment of the method of manufacturing the biological membrane includes the steps of transfecting cells with cDNA or cRNA encoding an ion channel of interest and cloning cells expressing the ion channel of interest. These steps provide the invention with the advantage of permitting studies of heterologously expressed cloned channels where the identity of the native channel is known or where precise knowledge is required of the interaction of compound structures and chemical moieties of the ion channel.

Preferably an embodiment of the method of manufacturing the perforated substrate comprises the steps of adjusting the profile, taper or diameter of the pore with a laser.

Preferably the laser source is controlled by an automated stage under control of a computer and inverted phase-contrast microscope which provides the advantage of permitting visual examination of the pore characteristics e.g. profile, taper and diameter.

Preferably an embodiment of the method of manufacturing the perforated substrate comprises other non-laser methods such as photo-etching, casting and physical piercing of the substrate.

Preferably an embodiment of the screening method comprises the step of measuring ion channel activity by monitoring trans-epithelial resistance measurements (TERM) across an intact cell layer.

In a further embodiment of the screening method a surface of the contiguous cell layer is preferably permeabilized thereby providing access to the interior of the cells. This has the great advantage of providing the means for current and voltage-clamping which is not possible with any existing high-throughput screening system. Not only does this permit high time-resolution recording but is also provides the means to stimulate or activate voltage-gated ion channels in a precise and controlled manner. For example, it is not necessary to alter the ionic composition e.g. by elevating $K^+$ to depolarize cells, which in itself can modulate the kinetics of ion channels (e.g. $K^+$ channels) and also obscure the activity of novel ligands by competition at ion channel binding sites. This is a very great advantage over all existing systems. Permeabilization also allows the introduction to the cytosol of compounds that otherwise could not do so either by virtue of molecular weight or physicochemical characteristics.

Preferably a surface of the contiguous cell layer is permeabilized by antibiotics selected from the group which comprises amphotericin and nystatin; or detergents selected from the group which comprises digitonin and saponin; or physical disruption using a high voltage field; or by enzymatic digestion of a part of the membrane using an appropriate enzyme thereby permitting intracellular voltage or current measurements to be made.

An advantage of using high voltage fields to permeabilize the membrane (electropermeabilisation) is that such a technique can permeabilize the plasmamembrane while sparing smaller intracellular structures such as mitochondria and endoplasmic reticulum. The technique can also be controlled very precisely and does not necessitate a facility to exchange solutions in a lower chamber of the recording apparatus.

Preferably an embodiment of the invention provides a screening method which includes the step of multiplexing up to 384 recording elements to a data acquisition system utilizing multiple voltage-clamp amplifiers. This has the advantage of providing extremely high time resolution and effectively simultaneous measurement from all wells. This has the advantage of providing the TERM system with the potential to achieve throughput rates similar to the best possible for conventional fluorescence-based ligand-receptor binding assays ($\geq$150,000 compounds per week).

Preferably an embodiment of the method of screening for the detection or assay of compounds with activity on ion channels of interest in an array of droplets on a porous substrate. An array of miniature recording chambers may be created by placing a 'lid' incorporating recording electrodes over the matrix of droplets such that a meniscus of droplet solution is established. A test compound in conducting solution is placed in at least one of the droplets or applied via access ports in the 'lid' and the resistance of the biological membrane or conductance (in voltage-clamp configuration) is measured under the influence of the test compound.

In an alternative embodiment of the screening method the biological membrane is placed in a plurality of chambers and test compound in physiological solution, or non-physiological solution comprising a solvent eg dimethyl sulphoxide, is added to the chambers.

Preferably an embodiment of the screening method comprises the steps of drug delivery and washing of the multi-well plate.

Preferably an embodiment of the screening method incorporates a step of stimulation of cells involving the use of a photoactivatible 'ion scavenger' eg of ions such as $K^+$. The active entity can be released by flashing the entire plate at once with a high intensity light source eg a laser or Xenon lamp. The advantage of this system is that membrane potential can be altered by altering the ionic distribution in a non-invasive fashion and with fine temporal control.

It has surprisingly been found that a biological membrane can be adhered with a high resistance seal to a perforated substrate for use in a high throughput screen for test compounds having activity on ion channels. This was considered unobvious to a person skilled in the art at the outset in view of the fact that achievement of a high resistance seal has not been possible without an undue burden. Furthermore, perforated substrates having a biological membrane sealed thereto have not been suggested for use in high throughput screens.

It has surprisingly been found that a biological membrane capable of adhering with a high resistance seal to a substrate may be constructed for use in a high throughput screen. Surprisingly it has been found that the biological membrane may be constructed having ion channels which are predominantly the ion channels of interest. Furthermore, it has surprisingly been found that a high throughput screen may be constructed and used to detect and assay a throughput of test compounds which may be in excess of 30000 per week.

Surprisingly the screen may be used to obtain bona fide electro physiological data relating to functional ion channel activity.

The biological membrane of the invention was unobvious at the outset to a person skilled in the art. Construction of a biological membrane having high resistance seals with a substrate such as perforated glass had not been achieved and was not considered possible without an undue burden. In addition construction of a membrane having ion channels which are predominantly an ion channel of interest had not been considered possible without an undue burden.

The high throughput screens and methods of the invention were unobvious at the outset to a person skilled in the art in view of the fact that it was not considered possible without an undue burden to screen the high throughput of test compounds which may be achieved by the invention.

In addition to the advantage of a high-throughput of test compounds, embodiments of the screen and method of the invention may provide functional assays (cf, say ligand binding) in which the mode of action (e.g. blocking or enhancing) of the test compound on voltage gated ion channels is measured via changes in membrane resistance or by recording the current flowing through ion channels in the membrane directly.

EXAMPLES

An embodiment of the screen of the invention comprises a multi well plate with integrated recording devices, by which means a massively parallel voltage clamp (MPVC) can be performed on a plurality of wells in a plate within short periods of time (ca. 1-60 s). Preferably commercially available 96 or 384 well plates are employed, or the 96 or 384 position array format is adopted.

An embodiment of the screen of the invention preferably provides a throughput of test compounds in excess of 30,000 per week with bona fide electrophysio-logical 'read-out' of functional ion channel activity. An embodiment of the screen may provide high resolution both in terms of time; for a 96 well plate, 1 ms/point/voltage clamp setup. The sensitivity to modulation of channel activity is $\geq$1%.

An embodiment of the present invention provides a method which comprises the steps of measuring transepithelial electrical resistance across a contiguous layer of cells expressing predominantly an ion channel of interest. It will be apparent to a person skilled in the art that the method depends on adherence of the cells to a substrate that allows formation of tight junctions between adjacent cells such that a high-resistance sheet is formed. Changes in activity of the ion channels expressed in the membranes of individual cells are reflected by changes in the resistance across the sheet as a whole. In a refinement of this embodiment of the invention, access to the interior of the cells comprising the sheet is obtained by means which permit population current and voltage clamp recording to be made.

Transepithelial resistance measurements have been carried out as follows:

a) Epithelial/Endothelial Type Cells.

The overall transepithelial resistance is composed of two principal components, the sum of the 'whole-cell' conductances of the individual cells making-up the pseudo-epithelium and the sum of the intercellular conductance pathways.

Naturally-occurring epithelial (and endothelial) cells form tight junctions with one another. This tight packing reduces the leakage of ions/solutes between cells, resulting in relatively low numbers of intercellular conductance pathways across the membrane as a whole. Thus, where conditions permit tight junctions to form, changes in the cell transmembrane conductance are measurable. One approach to this method was to select a host cell with appropriate growth properties. Cell-types which also express native ion channels at low levels are considered suitable for expression of cloned ion channels. A large hurdle for a person skilled in the art in this approach lay in obtaining cells in which the latter is true.

b) Transepithelial Resistance Measurement in Non-Epithelial Cells.

An alternative to the approach described above is to use non-epithelial cells that are known to express negligible numbers of ion channels of their own as a basic expression system for cloned cells which express ion channels of choice. There are several cell-types that fulfill this criterion. However, a large hurdle to a person skilled in the art was presented in that they do not form contiguous layers of cells in culture with tight junctions. In an embodiment of the invention there is provided a high resistance 'epithelial' layer in which this hurdle has been overcome.

Transepithelial Current Measurement (Massively Parallel Voltage Clamp (MPVC)

An embodiment of the invention was obtained by gaining access to the interior of cells in the 'epithelium' by disrupting or permeabilizing one face of each cell contributing to the cell layer. This has been carried out by chemical methods, for example by allowing certain types of antibiotics (e.g. amphotericin) or detergents (digitonin) to come into contact with one face of the cell surface or through physical disruption e.g. using high voltage fields (electroporation/integral zapper).

Electrical Recording Systems

A number of systems have been developed and they are outlined below:

Pilot Test Systems

Figure 1B:
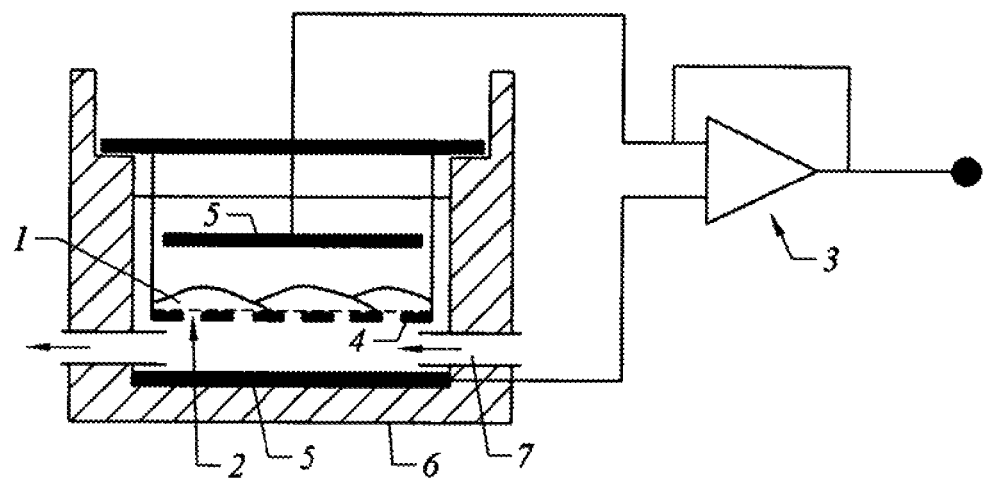
Figure 2A:
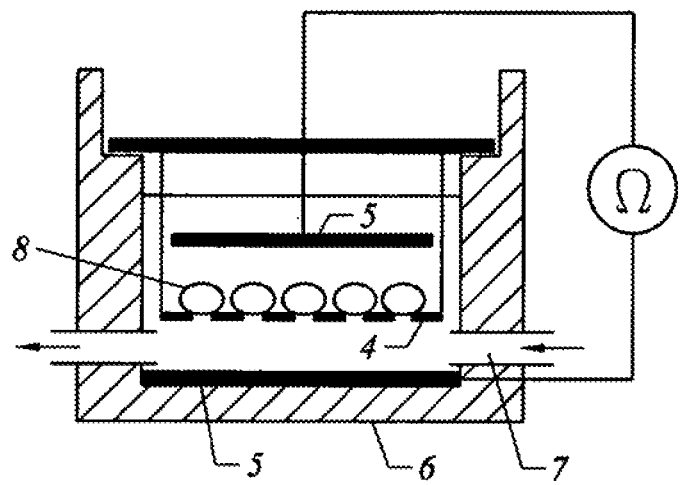
FIG. 2 shows an embodiment of the screen of the invention having a perforated substrate.
Figure 2B:
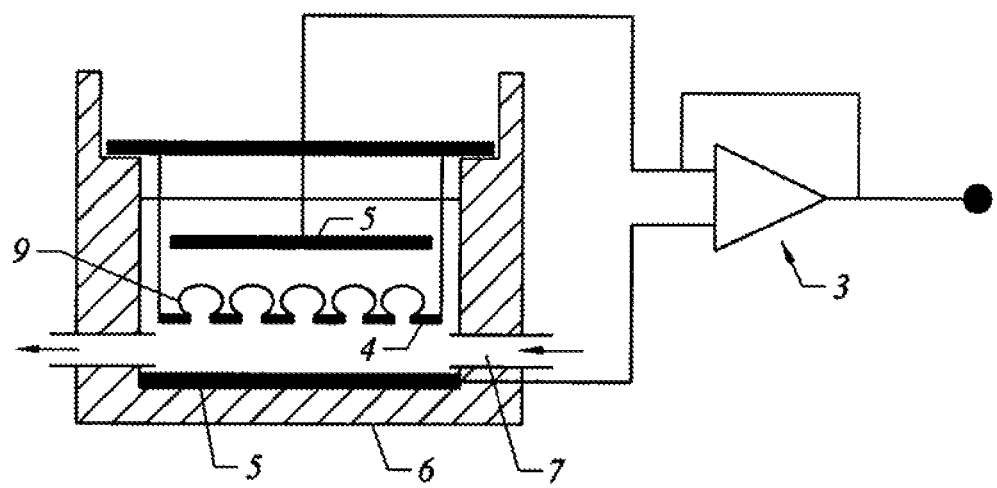

For pilot testing of the integrity of pseudo-epithelial layers, transepithelial resistance was measured using a chamber into which permeable tissue culture supports were inserted (FIGS. 1 and 2). Cells were grown in culture to confluency on this support. In the case of perforated substrates, the material (e.g. coverslip) was inserted in a purpose-built test rig which permitted variation in the pressure in the lower compartment and/or upper chamber and at the same time allowed resistance measurements to be made (FIGS. 1$a$ and 2$a$). To avoid polarization of the electrodes, an oscillating voltage signal was passed across the cell-layer via linear or circular electrodes positioned above and below the permeable support on which the layer of cells was growing and the impedance of the cell-layer was measured. In the case of permeabilized cell-layers (FIGS. 1$b$ and 2$b$), voltage and current-clamp recording was carried out using a voltage-clamp amplifier interfaced with a computer to control experimental protocols and sample the data.

Scale-Ups and Operational Systems

Figure 3:
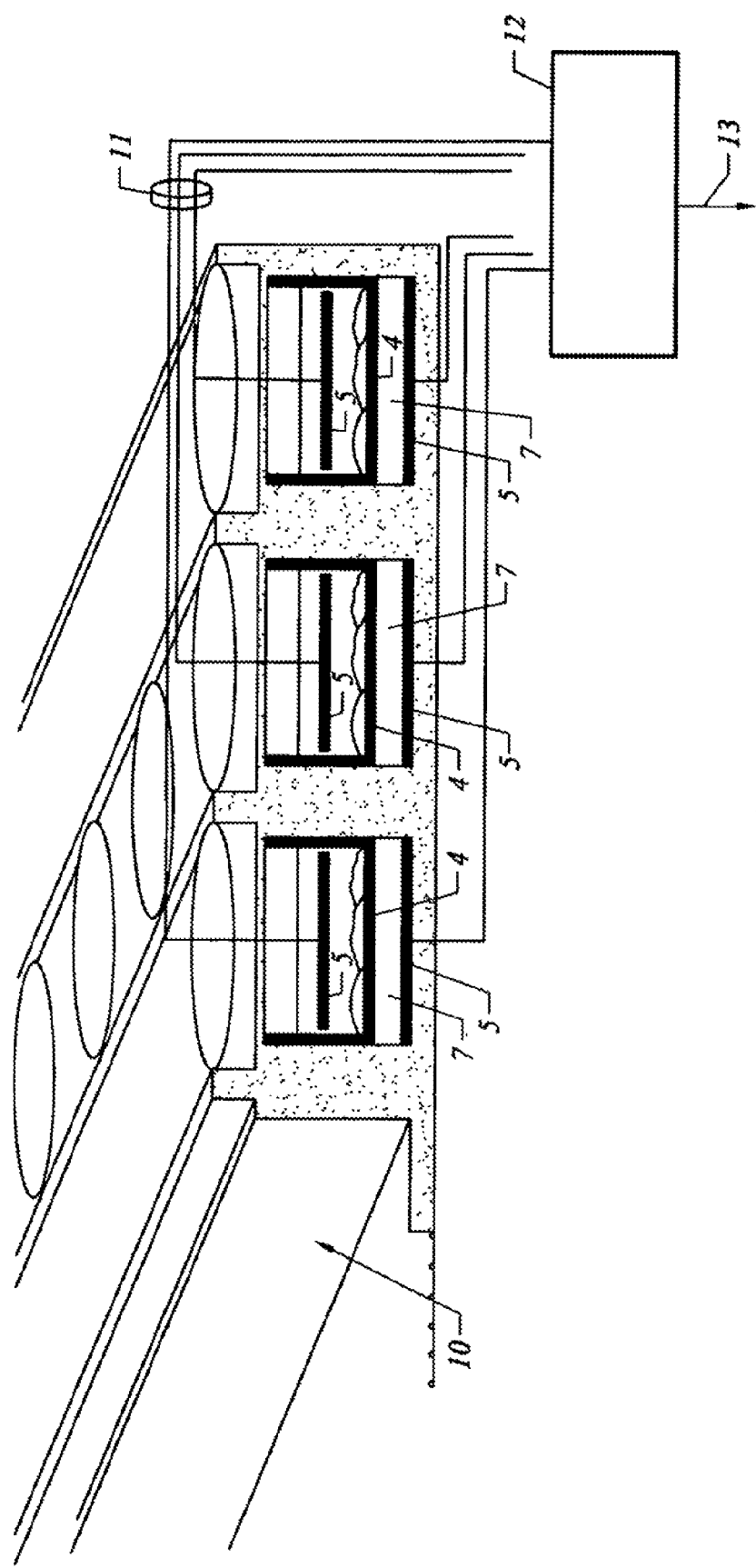
FIG. 3 shows adaption of a commercially available multi-well plate for use in a screen according to an embodiment of the invention. The figure shows an integral multi-recording electrode head cluster.
Figure 4:
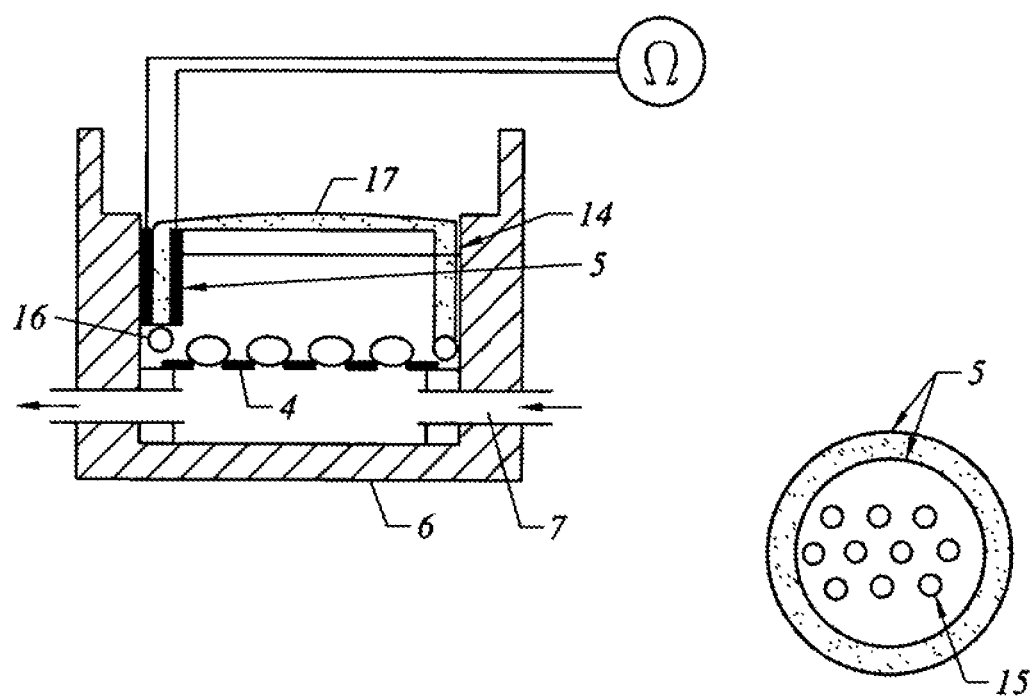
FIG. 4 shows an embodiment using a movable recording head wherein a single recording head reads single wells sequentially.

In either TERM or MPVC commercial screens utilize a multiwell plate measuring system (FIG. 3) or equivalent (e.g. using a droplet matrix generated using a nano litre piezo-dispenser). This was derived to some extent from the pilot test rig but required the design of an integral recording head of which embodiments of the invention include a number of possibilities. They are described below.

i) single recording head which reads single wells sequentially (FIG. 4).
ii) moveable linear row of recording heads (e.g. 12 for a 96 well plate system; 24 for a 384 well system) which are moved across the plate in 8 (96 well) or 16 (384 well) steps.
iii) electrode matrix built into the plate with multiplexing for recording headstage & acquisition system. For larger density plates multiple voltage-clamps were used to maintain sampling frequency and therefore time resolution (FIG. 3).
iv) droplet system (FIG. 5).

Multiwell Plate Adaptation

Embodiments of the screen of the present invention preferably include an integral automated pipettor in the working versions of TERM and MPVC.

Preferably embodiments of the screen of the invention include a facility for washing recording heads between use in separate rows.

According to an embodiment of the invention the method of manufacture of the biological membrane comprises the steps of obtaining a high resistance seal with perforated glass substrate (or other support) and/or the step of obtaining a cell-line having the ability to form sheets and having low or negligible numbers of native ion channels.

Epithelial Cell Approach

Naturally occurring cell-lines and engineered cell-lines have been developed. They are described below.

Naturally-Occurring Cell-Lines

Cell-lines referred to in the literature have been evaluated for 'off the shelf suitability. Initial candidates included ECV-304, RBE4 and C6 glioma cells. Criteria for use were:

a) ability to form contiguous layers of cells with tight junctions; transepithelial resistance of 3125 $\Sigma cm^{-2}$.

b) low to negligible numbers of background voltage-gated ion channels as assessed by whole cell patch clamp by standard methods. Preferably the conductance level is #2 nS per cell.

Engineered Cell-Lines

A suitable cell-line may be prepared by molecular engineering. If background conductances of the naturally-occurring cell-lines were above the threshold given in (b) above, the cell-line was assessed for possible gene knock-out to engineer a novel host cell.

Artificial Epithelia

Perforated Substrates

Perforated substrates have been developed as set out below:

Laser-Generated Substrates a) Prototypes

Glass coverslips were perforated in a sequential fashion (1 hole at a time) using a laser energy source in conjunction with automated stage under computer control and an inverted optics microscope. This permitted prototypes to be constructed with fine control of parameters such as focal area, laser power and time of exposure. The ability to achieve high resistance sealing between cells and substrate was tested using coverslips created in this way.

Grid patterns were reproducibly generated in variable formats by means of a computer-controlled stage which was interfaced with the laser via the computer. Coverslips of various materials including glass (as well as plastics and other biocompatible materials) were used. Their diameters were 1 Omm (96 well plate) or 5 mm (384 well plate); and of variable thickness (ca.1-20 µm). Pores were generated with diameters varying between 0.5µ and 10µ. The profile of the pore, its taper and internal and external diameters were evaluated to optimise sealing with the test cells. It is important to establish the appropriate level of smoothness of the pore. Pore density was optimized for signal-to-noise characteristics, fidelity of voltage-clamp recording and statistical considerations.

To encourage sealing between cell and pore, a number of approaches were taken (FIG. 1). They are outlined below:

i) negative pressure in lower liquid compartment e.g. using a venturi effect caused by flowing solution across the ventral orifice and/or by supplying the flowing solution at a reduced overall pressure.

ii) positive pressure in the upper liquid compartment iii) coating of the coverslip with anti-adhesion material that is burned off in the pore region during the pore manufacturing process (i.e. laser induced pore formation)

iv) facility to jog or vibrate coverslip to encourage cells to 'find' pores before adhering to the substrate at non-pore locations v) either a coverslip carousel or multiwell plate carousel to permit centrifugation.

vi) application of voltage field across pores to move cells into pore mouth.

Figure 7:
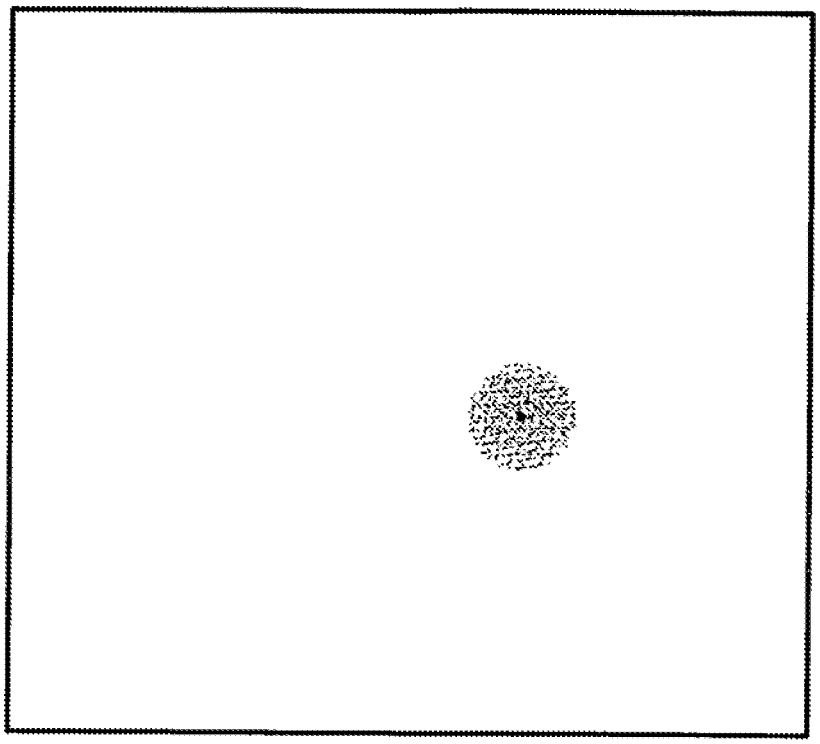
FIG. 7 shows a pore formed in a substrate, according to the invention. The light micrograph shows a pore in a thin glass substrate. The pore, which was approximately 2 micrometers in diameter, was manufactured by using pulses of focussed laser energy followed by a combination of fire polishing and plasma modification. The scale bar is 10 micrometers across.

Surprisingly, laser induced pore formation provided remarkable results. FIG. 7 shows a typical pore produced by this method. When physiological solutions were added to either side of the pore, trans-substrate resistances, typically in the range 200 kOhms to 400 kOhms, were routinely observed. With the addition of cells, the observed resistance was approximately double this figure. With the additional application of one or more of the approaches outlined above, resistance measurements approaching the gigaohm range were observed.

b) Scale-Ups

Bulk perforation and simultaneous recording (sealing) were evaluated. The approach comprised 'flashing' the whole bottom surface of a multiwell plate (or equivalent matrix) with a high energy laser source. With appropriate well structure, the precise location of the required pores was known and with appropriate titration of cell density, a high probability of a having a cell 'in residence' was achieved. The plate was perforated and the ventral cell surface breached almost simultaneously. This required a much higher energy laser than that used in prototypes (above).

c) Cell-Types

Although Chinese hamster ovary (CHO) cells have been used to develop the invention, it will be apparent to a person of ordinary skill in the art that a wide variety of cell-lines and primary cells such as neurones isolated from intact tissues may be employed.

Other Perforation Methods

Alternative methods of perforating glass coverslips and other materials have been evaluated such as etching, casting glass or plastics sheets.

Porous Rubber

Porous rubber substrates are commercially available for growing cells in cell-culture. The porosity has been evaluated in the context of the resistance and current-measuring applications described herein.

Other Materials

It will be apparent to a person skilled in the art that additional materials such as PTFE, PETP etc. may be employed in accordance with the present invention. These have the advantage of having high dielectric constants but also of being manufactured in extremely thin sheets. This has the advantage of reducing the minimum series resistance in the whole system and also facilitating the introduction of exogenous substances to the cell cytosol.

Multi-Well Plate Recording Apparatus

The basal multi-well plate recording apparatus preferably accommodates a 96-well/location format. Preferably multiples of the 96-well format are constructed with a minimal expansion to 384 well format. An advantage of increasing well-density is that the amount of test compound used is reduced and fewer plates are used with concomitant reductions in ancillary running costs per compound tested.

The following two approaches have been evaluated:— a) A TΣRM workstation designed to interface with commercially-available robots and plate processors.

b) Fully integrated stand-alone system which provides plate handling, solution changes and recording headstages.

Fluid Matrix System

Figures 6A, 6B, 6C, 6D:
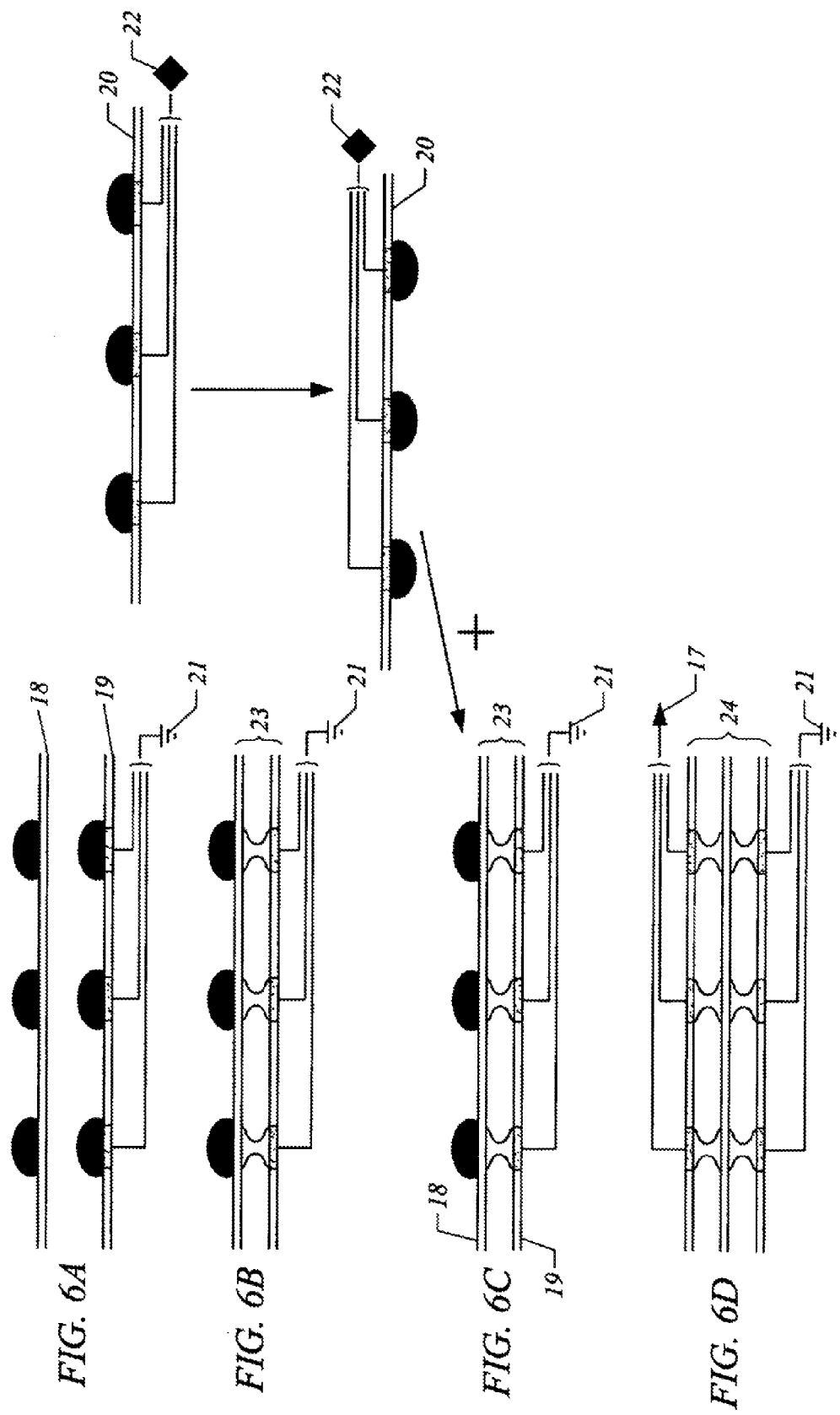
FIG. 6 shows a further embodiment of a fluid matrix system wherein multiple arrays of droplets are sandwiched together.

An array of miniature recording chambers were created by dispensing droplets containing a suspension of cells onto the recording substrate in a predetermined pattern and density (see FIG. 5). The substrate can be of any of the types described above e.g. perforated glass, plastic, rubber, etc. The complete recording configuration is accomplished by placing a 'lid', or moveable recording head, incorporating recording electrodes over the matrix of droplets such that a meniscus of the droplet solution is established as exemplified in FIG. 5. An array of droplets may also be generated on the reverse of the porous substrate to provide a conducting pathway to at least one reference electrode and also the means by which substances may be applied to the lower surface of the substrate and hence cell membranes. Similarly, reagents can be applied via a further droplet matrix applied to the 'recording plate' as shown in FIG. 6. Drug solutions may be dispensed onto a recording "head" plate; the plate may then be inverted; and the inverted plate may then be docked with the cell matrix to bring the drug into contact with the cells. The advantage of this approach is that sheets of substrate can be designed without the need to transfer substrate discs to multiwell plates and also obviates complex chamber design with seals, 'O'-rings and the like. The invention can still accommodate addition of solutions and has the additional advantage of using very small volumes and thus small quantities of reagents and cells.

What is claimed is:

1. An apparatus for patch clamping measurements to detect and assay compounds with ion channel activity in a biological cellular membrane, comprising:
    a well with a porous substrate disposed therein, said substrate having at least one pore with a diameter between 0.5 μm and 10 μm;
    a solution perfusion channel disposed below said porous substrate and defining an inlet and an outlet for flow of fluid containing said compounds therethrough;
    a first electrode disposed in said well; and
    a second electrode disposed in said solution perfusion channel in electrical communication with the first electrode through said porous substrate.

2. The apparatus of claim 1, wherein said substrate is configured to permit adherence of a biological cellular membrane on an upper side thereof opposite said perfusion channel with a seal between said cellular membrane and said porous substrate having sufficient electrical resistance to facilitate patch clamping measurements across said membrane.

3. The apparatus of claim 2, wherein said seal is a high resistance seal.

4. The apparatus of claim 2, further comprising a biological cellular membrane adhered only to said upper side of the porous substrate with a high resistance seal.

5. The apparatus of claim 1, further comprising a voltage-clamp amplifier connected between said electrodes and configured for said patch clamping measurements.

6. The apparatus of claim 1, wherein said at least one pore has a diameter between 1 and 7 μm.

7. The apparatus of claim 6, wherein said at least one pore has a diameter of 1-2 μm.

8. The apparatus of claim 1, wherein said at least one pore is formed by a laser.

9. The apparatus of claim 4, wherein a pressure differential is applied across the substrate such that a lower pressure exists in the solution perfusion channel as compared to in the well above the substrate.

10. The apparatus of claim 1, further comprising a plurality of said wells.

11. The apparatus of claim 10, wherein said plurality of said wells are formed in a multi-well plate.

12. The apparatus of claim 11, wherein said first electrode is disposed on a moveable recording head that is moveable between the wells of the multi-well plate.

13. The apparatus of claim 12, wherein said movable recording head includes plural first electrodes such that more than one of said wells of the multi-well plate may be contacted with each movement of said recording head.

14. The apparatus of claim 11, wherein said porous substrate in each said well includes plural pores.

15. The apparatus of claim 1, wherein said porous substrate includes plural pores.

16. An apparatus, comprising:
a plate defining a plurality of wells;
a porous substrate disposed in a bottom of each said well, wherein the substrate in each well defines at least one pore with a diameter between 1 µm and 7 µm, and is configured and dimensioned to permit adherence of a biological cellular membrane on an upper side thereof with a high resistance seal between the membrane and said porous substrate having sufficient electrical resistance to facilitate patch clamping measurements across a biological membrane adhered to said substrate for detecting ion channel activity in the membrane;
a solution perfusion channel disposed below the porous substrate of each said well, said channel defining an inlet for flow of fluid therethrough across said pores and an outlet;
at least a first electrode disposable in each said well; and
at least a second electrode disposed in said solution perfusion channel in electrical communication with said first electrode across the porous substrate.

17. The apparatus of claim 16, wherein the porous substrate in each said well defines plural pores.

18. The apparatus of claim 16, wherein the porous substrate is glass, PTFE or PTEP and said pores are laser formed.

19. The apparatus of claim 16, wherein said at least one pore has a diameter between 1µ and 2µ.

20. The apparatus of claim 16, further comprising a voltage-clamp amplifier connected between said electrodes and configured for patch clamping measurements.

21. The apparatus of claim 1, further comprising a solution containing said test compound disposed within said solution perfusion channel.

* * * * *